US011639488B2

(12) United States Patent
Dalle et al.

(10) Patent No.: US 11,639,488 B2
(45) Date of Patent: May 2, 2023

(54) PHOTO BIOREACTOR

(71) Applicant: SUEZ INTERNATIONAL, Paris la Defense (FR)

(72) Inventors: Marie-Alix Dalle, Grenoble (FR); Jérôme Arnaudis, Paris (FR)

(73) Assignee: SUEZ INTERNATIONAL, La Défense (FR)

(*) Notice: Subject to any disclaimer, the term of this patent is extended or adjusted under 35 U.S.C. 154(b) by 306 days.

(21) Appl. No.: 16/771,522

(22) PCT Filed: Dec. 19, 2018

(86) PCT No.: PCT/EP2018/085867
§ 371 (c)(1),
(2) Date: Jun. 10, 2020

(87) PCT Pub. No.: WO2019/121933
PCT Pub. Date: Jun. 27, 2019

(65) Prior Publication Data
US 2021/0179987 A1 Jun. 17, 2021

(30) Foreign Application Priority Data
Dec. 22, 2017 (FR) ...................................... 1762943

(51) Int. Cl.
*C12M 1/00* (2006.01)

(52) U.S. Cl.
CPC ............ C12M 21/02 (2013.01); C12M 29/08 (2013.01)

(58) Field of Classification Search
CPC ...... C12M 1/002; C12M 31/00; C12M 29/08; C12M 27/24; C12M 21/02; C12M 23/26; C12M 23/24; C12M 31/10; C12M 23/06; C12M 31/08
See application file for complete search history.

(56) References Cited

U.S. PATENT DOCUMENTS 4,952,511 A    8/1990   Radmer

FOREIGN PATENT DOCUMENTS

| CN | 1 483 807 A | 3/2004 | |
| CN | 1483807 A * | 3/2004 | ............ C12M 21/02 |
| EP | 1 169 428 A1 | 1/2002 | |
| WO | 00/61719 A1 | 10/2000 | |
| WO | 2013/079948 A1 | 6/2013 | |
| WO | WO-2013079948 A1 * | 6/2013 | ............ C12M 21/02 |
| WO | 2014/044883 A1 | 3/2014 | |

OTHER PUBLICATIONS

Pruvost, et al., "Industrial production of of microalgae and cyanobacteria", Chimie verte et nouvelle gestion de'énergie, Editions T.I., Internet Reference: CHV4030, 2017, 4 pages.
Database WPI, Thomson Scientific, XP002784807, 1 page, 2017.

* cited by examiner

Primary Examiner — Aaron J Kosar
(74) Attorney, Agent, or Firm — BakerHostetler

(57) ABSTRACT

A photobioreactor includes a first and a second container extending along a longitudinal direction; the second container extending inside the first container, so as to delimit a first channel between the first and the second containers; and forming a second channel inside the second container; a first passage means capable of allowing the circulation of a fluid between the first channel and the second channel; a second passage means capable of allowing the circulation of the fluid between the first channel and the second channel, disposed above the first passage means; at least one light source; a gas injection means, configured so as to inject gas in the form of bubbles into the second channel; the circulating fluid being able to be exposed to a light source.

19 Claims, 8 Drawing Sheets

PHOTO BIOREACTOR

CROSS-REFERENCE TO RELATED APPLICATIONS

This application is a National Stage of International patent application PCT/EP2018/085867, filed on Dec. 19, 2018, which claims priority to foreign French patent application No. FR 1762943, filed on Dec. 22, 2017, the disclosures of which are incorporated by reference in their entirety.

FIELD OF THE INVENTION

The invention lies in the field of photobioreactors.

More particularly, the invention relates to an intensive production photobioreactor, suitable for avoiding a reduction of the diffusion of light to the algal solution disposed in the photobioreactor.

Photosynthetic microorganisms of micro-algae type tend to be necessary in many application sectors. The photosynthetic microorganisms are thus used for the solar production of bioenergies, the production of natural molecules of interest or even the depollution of gaseous effluents (for example the $CO_2$ from smoke) or liquids with production associated with a plant biomass with multiple outlets (PRUVOST, Jeremy and CORNET, Jean-Francois and LE BORGNE, Francois and JENCK, Jean, 10 Feb. 2017, "Production industrielle de microalgues et de cyanobactéries" [Industrial production of microalgae and of cyanobacteria], Chimie verte et nouvelle gestion de l'énergie, on line, Editions T.I., 2017.

Regarding the $CO_2$ gas depollution technologies, the concepts of carbon sink or of carbon dioxide ($CO_2$) sink come into play: these concern a reservoir, natural or artificial, which absorbs carbon from the atmosphere and contributes to reducing the quantity of atmospheric carbon dioxide. The photosynthetic microorganisms of the micro-algae type are of particular interest for this application.

The industrial production of photosynthetic microorganisms requires dedicated technologies that make it possible to conduct culture processes called photo-processes that can allow the photosynthetic growth based on assimilation, by virtue of captured light, of inorganic nutrients and minerals. Depending on the operating constraints and objectives, the culture process can be conducted by using a wide panel of technological solutions ranging from open systems (open basin type, for example shallow ponds exposed to the light of the sun) to closed systems and using either solar energy, or an artificial light source. These are generically called photobioreactors.

The photobioreactors must make it possible to achieve high productivities of photosynthetic microorganisms. The aim is therefore to optimize their operation to maximize the performances thereof.

The open systems have a major drawback of being subject to contaminations through dust, other microorganisms, insects and environmental pollutants. Furthermore, it proves difficult to control the processes in open basins.

The closed systems generally comprise long pipes forming a circuit that is set out to allow a maximum exposure of an algal solution flowing in the pipes to the light. They also allow the placement of a fine layer of culture in suspension allied with a biological purity in order to cultivate the microorganisms in the best possible way. Many systems with different forms and functions have been developed with the aim of cost-effectiveness on an industrial scale.

The photobioreactors are however subject to many meteorological events. For example, the natural light of the sun is not available during the night and would not be sufficient during meteorological events such as a cloudy sky. Furthermore, the natural light is not sufficient to establish an intensive microalgae culture. Other light sources have been used to overcome these drawbacks.

Furthermore, the cleaning of the pipes has to be managed, based on the materials used, and based on the microorganisms generated, and this has to be done in such a way as to allow the light to be diffused correctly in time.

As an example, the U.S. Pat. No. 4,952,511 describes a photobioreactor for photosynthetic microorganism culture which uses a light reservoir or light cavity to distribute a light of high intensity and uniformly in a tank comprising microbic liquid culture compartments. In order to achieve such an objective, the light compartment needs to have at least one transparent wall including a part extending in the tank.

A photobioreactor as described in the U.S. Pat. No. 4,952,511 is designed to diffuse the light in the microbic liquid and the diffusion of the light inside the tank can thus be optimized by reducing the thickness of the walls of the culture tanks.

Conversely, a significant thickness of the walls of the tank has the effect of reducing the intensity of the light.

Furthermore, a high turbidity value, reflecting a turbulent algal solution, and a high concentration of organic material and/or of microorganisms in the algal culture have the effect of reducing the intensity of the light.

A simple solution for maintaining a diffusion in the unfavorable conditions presented above would be to increase the light intensity, beyond the light intensity that is needed in a clear solution, so as to maintain an absorption that is favorable for the phototrophic microorganisms. Thus, the light intensity must be sufficient even after its attenuation through the thickness of the tank, and/or after having passed through a given distance in turbulent solution, concentrated with organic matter and/or microorganisms.

One drawback with such a solution is that it risks being done to the detriment of the cost-effectiveness of the system (more light intensity has to be expended).

Furthermore, it risks burning the floating algae, notably the algae situated closest to the wall (the less distance the light emission has passed through the solution, the more intense it is, so this has the drawback of treating the solution in a non-uniform manner) and/or causing them to precipitate. Such phenomena are counter-productive because the burnt and/or precipitated algae do not participate in the development of the system: in effect, they do not consume the added nutrients, do not metabolize them. They also participate in making the water more turbid and can aggregate in the system, thus risking clogging all or part of the reactor.

Conversely, an insufficient light intensity tends to attract the algae to the walls of the pipes or tanks, blocking even more the access of the light beyond a layer formed on the internal wall of the tanks.

Furthermore, when the algal density within the solution increases, it thereby reduces the distance of penetration of the light in the reactor, and therefore the period of light intensity to which the algae are subjected.

The aim is therefore to find a solution to subject an optimal and uniform light intensity to the algal solution, and to do so regardless of its turbidity, its algal density and its concentration of organic matter and/or of other microorganisms.

The European patent EP1169428 discloses a photobioreactor with an improved exchange surface resulting in a better spatial distribution of the light in the reactor and thus an optimization of the intensity of the light in the reactor. Thus, the subject matter of the invention of the patent EP1169428 is a tank of rectangular cross section having a larger exchange surface than a tank of circular cross section. The patent relates also to a means for guiding turbulent flows, allowing for a "flashlight effect" obtained by increasing the turbulence. This effect is based on the principle that the algal cells can, during dark phases, metabolize the energy that they have accumulated during the light phases. This effect is created when the algal cells are exposed to a significant light intensity and at a short distance from the walls of the reactor during the light phase. A cycle comprising a light phase and a dark phase must be no more than one second.

However, such a photobioreactor will lead to a rapid and probably uniform increase in said reactor of the algal density because of the strong light availability. Thus, the diffusion of the light in the algal culture will be affected by the creation of dark zones at the center of the culture tank and the algal growth will ultimately be reduced.

The lack of availability of light for the algae therefore creates phenomena that risk emphasizing even more the lack of availability, thus creating a vicious circle.

In particular, in an intensive production reactor, the algal growth is strong and induces an increase in the algal density. This increase causes the diffusion of the light in the medium to diminish, a consequence which in turn induces dark zones where the algal growth will be reduced. These dark zones will in turn lead to an attraction of the algae for the lightest walls of the tanks, which reduces the exchange surfaces and again reduces the diffusion of the light. Furthermore, the algae undergo a stress through lack of light, affecting the cost-effectiveness of the system.

There is thus a need for a photobioreactor which overcomes these drawbacks, while allowing for an intensive production, a device which avoids the reduction of the algal growth resulting from the reduction of the diffusion of the light, and/or from an increasing algal density, and/or from the attraction of the algae for the walls of the tanks.

A photobioreactor that allows for the most uniform possible diffusion of the light to the algal liquid is notably sought.

SUMMARY OF THE INVENTION

One object of the invention making it possible to achieve this aim is a photobioreactor capable of containing at least one fluid, characterized in that it comprises:
- a first container extending along a first longitudinal direction;
- a second container extending along a second longitudinal direction;
- the second container extending inside the first container, so as to delimit a first channel between an internal lateral surface of the first container and an external lateral surface of the second container; and forming a second channel inside said second container;
- at least one first passage means capable of allowing the circulation of the fluid between the first channel and the second channel;
- at least one second passage means capable of allowing the circulation of the fluid between the first channel and the second channel, and disposed above the at least one first passage means;
- at least one light source;
- a gas injection means, configured so as to inject a gas in the form of bubbles into the second channel;
- the first and second containers, the first and second passage means and the injection means being configured so as to allow a circulation of the fluid in the photobioreactor between the first channel and the second channel, and the circulating fluid being able to be exposed to the at least one light source.

There can be more than one second container: in this case, there is more than one second channel, and the first channel is formed by the space contained between the internal lateral surface of the first container and the external lateral surfaces of the second containers.

Throughout the present application, the first and second containers extend respectively along a first and a second longitudinal directions.

Throughout the present application, the terms "bottom", "top", "vertical", "horizontal", "below" and "above" are to be understood by taking a vertical longitudinal direction as reference, it being understood that each longitudinal direction may not be vertical, but be horizontal or inclined by another angle.

Throughout the present application also:
- "container" is understood to mean a hollow object intended to receive solid, liquid or gaseous products, delimited by at least one lateral surface. The object may not have bottom and/or top closure;
- a "first passage means" can also be called "bottom passage means";
- a "second passage means" can also be called "top passage means";
- "external lateral surface" (or "internal lateral surface") is understood to mean the surface extending in the longitudinal direction and delimiting an object on its outermost periphery, (or on its innermost periphery). If the object comprises several walls, the external lateral surface will be the external surface of the off-center wall, and the internal lateral surface will be the internal surface of the most centered wall.
- The terms "internal" and "external" should be understood in relation to a radial direction, relative to the longitudinal direction;
- "circumferential ring" is understood to mean a ring disposed on a circumference of a container, preferably cylindrical;
- "notched" is understood to mean a set of horizontal segments, alternately low and high, connected by vertical segments, the low segments forming the solids (or protuberances) and the high segments forming the voids (or depressions);
- "bottom part" should be understood to mean the part of an element comprising the bottom end of said element and possibly extending above said bottom end;
- "top part" should be understood to mean the part of an element comprising the top end of said element and possibly extending below said top end;
- "channel" is understood to mean a hollow form capable of allowing and guiding the flow of a fluid;
- "substantially circular" is understood to mean a closed curve practically defining a circle of radius r, with a standard deviation on the radius of +/−10% of the radius.

The fluid contains microorganisms, for example microalgae. It can also be a mixture of fluid and of solids. Furthermore, the fluid can be mixed with the injected gas or with the injected gas/solid mixture.

The inventors have been able to highlight a significant technical effect of the invention which makes it possible to improve the exposure of the microorganisms (for example the microalgae) to the light: the bubbles injected and circulating with the fluid diffract the light that they receive, the light is thus better distributed inside the photobioreactor.

Thus, the photobioreactor according to the invention makes it possible to solve the problem of allowing an intensive production, while avoiding the reduction of the algal growth resulting from the reduction of the diffusion of the light, and/or an increasing algal density, and/or the attraction of the algae for the walls of the tanks.

In other words, the circulation of the fluid and of the bubbles which drive the fluid, coupled with the diffusion of a light source, makes it possible to increase the exposure of the microalgae to the light.

That allows for the most uniform possible diffusion of the light to the algal liquid.

The air injection system, through the formation of bubbles and the driving of the fluid, creates a high shear rate in the medium, homogenizing the medium, preventing the algal deposits on the walls, and enhancing the contact between the micro-algae and the nutrients for said micro-algae and the $CO_2$.

According to one embodiment, the first container is closed at its bottom and top ends.

That has the advantage of being able to better manage the pressure of the gas injected into the photobioreactor, the temperature of the fluid, and, when the injected gas comprises $CO_2$, preventing the reduction of the $CO_2$ concentration. Furthermore, this is also often important for safety reasons, in order to prevent access to the fluid that can be contained in the photobioreactor.

According to an advantageous embodiment, the first and second longitudinal directions of the first and second containers are parallel, preferably coinciding.

According to a particularly advantageous embodiment, the first and second containers are first and second cylinders of revolution, preferably concentric.

The advantage of these two embodiments is that the width of the first channel is better divided up between the two containers along the longitudinal direction. Thus, the circulation of the fluid is more regular and less subject to the risk of jerks.

In particular, when the cylinders are concentric, a symmetry is obtained which makes it possible to obtain a width of the first channel that is regular between the two containers along the longitudinal direction. That allows for an even more uniform circulation of the fluid in the photobioreactor, improving the exchanges and notably avoiding dead zones and/or the risks of concentrations of algae at certain points of the photobioreactor.

Furthermore, the cylinder of revolution form makes it possible to avoid the dead zones which are zones of loss of retention of matter, and consequently notably more difficult to clean.

Alternatively, only one out of the first container and the second container is a cylinder of revolution.

According to one embodiment, the at least one first passage means is formed by apertures in the wall of the second container, preferentially in the bottom part of said second container.

According to a particular embodiment, the second container is a second cylinder of revolution and comprises a plurality of apertures forming first passage means, disposed along at least one second circumferential ring in the wall of said second container, and preferentially in the bottom part of said second container.

According to a particular embodiment, the apertures are disposed along several first circumferential rings in the wall of the second cylinder.

If the second container comprises several walls, the apertures must be formed in all of the walls in order to allow the passage of the fluid between the first and second channels.

Alternatively or in addition, the at least one first passage means can be formed by notches, preferentially disposed at the bottom end of the second container.

Any first passage means must allow suction of the fluid from the first channel to the second channel, while avoiding the diffusion of bubbles emitted in the second channel to the first channel.

The apertures and/or the notches can advantageously be dimensioned to ensure this dual constraint.

According to one embodiment, the at least one first passage means is formed by a height difference between the first container and the second container, the bottom end of the second container being situated above the bottom end of the first container.

This embodiment makes it possible to easily adapt the dimensions of the first passage means, notably as a function of the geometries of the photobioreactor, of the characteristics of the algal liquid and/or of the injected gas and notably of the sizes of bubbles in order to optimize the circulation of the fluid.

According to one embodiment, the at least one second passage means is formed by a height difference between the first container and the second container, the top end of the second container being situated below the top end of the first container.

This embodiment makes it possible to easily adapt the dimensions of the second passage means, notably as a function of the geometries of the photobioreactor, of the characteristics of the algal liquid and/or of the injected gas and notably of the sizes of bubbles in order to optimize the circulation of the fluid.

Alternatively or in addition, a second passage means is formed by apertures in the wall of the second container, in the top part of said second container.

According to one embodiment, the second container is a second cylinder of revolution and the apertures are disposed along at least one second circumferential ring in the wall of said second container, and in the top part of said second container.

If the second container comprises several walls, the apertures must be formed in all of the walls in order to allow the passage of the fluid between the first and second channels.

Alternatively or in addition, the at least one second passage means can be formed by notches disposed at the top end of the second container.

According to one embodiment, the injection means is able to generate bubbles of average diameters, preferentially less than or equal to 1 mm.

That makes it possible to obtain a better rate of dissolution of the $CO_2$ in the fluid, and a better mixing of the fluid, resulting notably in making best use of the technical effect of diffraction of the light by the bubbles within the algal liquid.

According to one embodiment, the injection means is able to inject a gas/solid mixture. That is particularly necessary to treat a gas/solid mixture injected into the photobioreactor: the mixture can notably comprise fine particles contained in the gas to be treated.

According to one embodiment, the injection means is disposed below the second container.

According to one embodiment, the injection means comprises a membrane, preferably disposed inside and in the bottom part of the second container. The function of such a membrane is to inject the gas in the form of bubbles of controlled and/or gauged size(s).

According to another embodiment, the injection means can comprise a diffuser of fine bubbles, a hydro-injector, porous stone or any other means capable of fulfilling the function of injecting the gas in the form of bubbles of more accurately controlling the size or sizes of said bubbles.

According to an advantageous embodiment, at least one light source comprises at least one lighting wall out of at least one wall of the first and second containers. That allows for a better uniformity of the light diffusion, without disturbing the flow of the fluid (no added dead zone).

According to one embodiment, the at least one light source comprises at least one first light source disposed inside the second container.

According to one embodiment, the at least one light source comprises at least one second light source disposed between the first container and the second container.

According to one embodiment, at least one light source is disposed on a bottom lateral surface of the second container.

According to one embodiment, at least one light source is disposed on an external lateral surface of the second container.

According to one embodiment, at least one light source is disposed on an internal lateral surface of the first container.

According to one embodiment, the at least one light source comprises at least one third light source disposed outside the first container, for example on an external lateral surface of the first container, or at a given distance from said first container.

According to one embodiment, at least one light source is formed by at least one light column extending along one out of the first and second longitudinal directions of the first and second containers.

The term light tube will also be applied hereinafter in the present description.

According to one embodiment, at least one light source comprises a coil having a helical form about an axis parallel to one out of the first and second longitudinal directions of the first and second containers, the coil being preferentially wound around the first and/or the second container.

According to one embodiment, at least one light source comprises LEDs.

According to one embodiment, the photobioreactor also comprises at least one recirculation pump configured to circulate the fluid from the bottom part of the photobioreactor to the top part of the photobioreactor.

According to one embodiment, the photobioreactor comprises at least one propeller.

According to one embodiment, at least one propeller is disposed in the bottom part of the photobioreactor, preferably in the second channel.

According to one embodiment, at least one propeller is disposed in the first channel.

According to one embodiment, at least one wall of the first container is transparent to the light.

According to one embodiment, at least one wall of the second container is transparent to the light.

BRIEF DESCRIPTION OF THE DRAWINGS

Other features and advantages of the invention will become apparent from the following description given as an illustrative and nonlimiting example, in light of the attached drawings in which.

DETAILED DESCRIPTION

Figure 1:
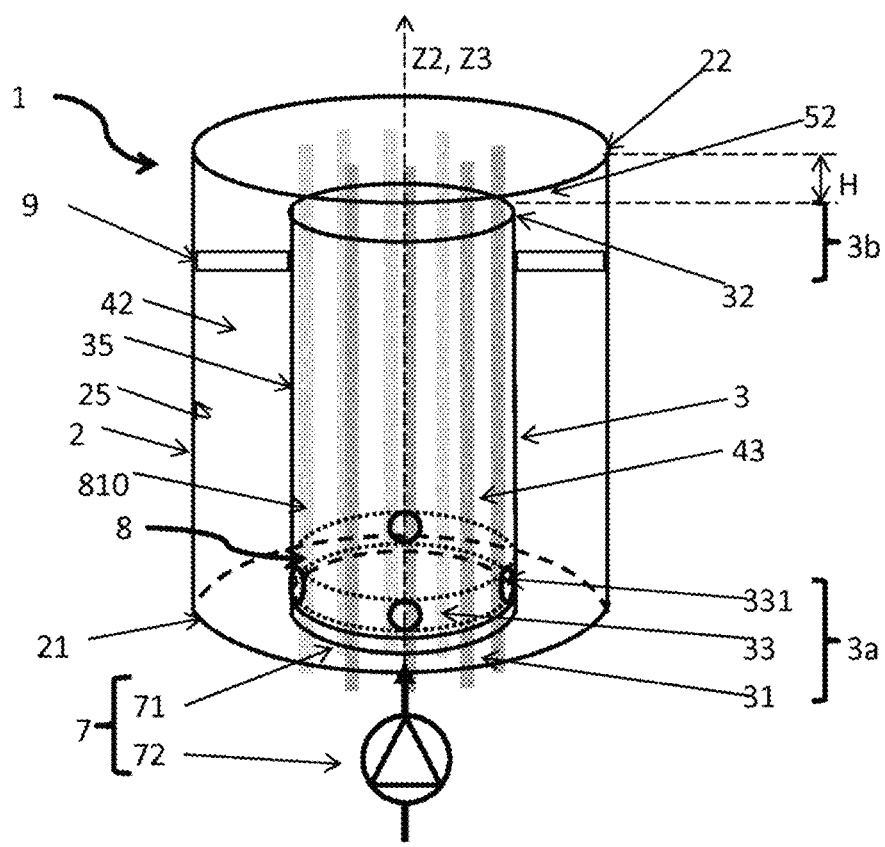
FIG. 1 illustrates a photobioreactor according to a first embodiment.

FIG. 1 illustrates a photobioreactor 1 according to a first embodiment.

The photobioreactor 1 comprises a first container 2 which is a first hollow cylinder extending along a first longitudinal direction $Z_2$ and a second container 3 which is a second hollow cylinder extending along a second longitudinal direction $Z_3$ and disposed inside the first hollow cylinder 2. The two cylinders are cylinders of revolution. The axes of revolution of the first and second cylinders coincide, in other words, the cylinders are concentric. The space between the two cylinders forms a first channel 42. The space in the second cylinder 3 forms a second channel 43.

The first bottom end, or base 21, of the first cylinder 2, closes the bottom end of the photobioreactor 1.

The second bottom end, or base 31, of the second cylinder 3 can coincide with the base 21 of the first cylinder 2.

The photobioreactor 1 can advantageously comprise means 9 for fixing the second cylinder 3 and/or positioning it relative to the first cylinder 2, for example so that the first channel 42 formed between the two cylinders is of stable form.

The at least one first passage means comprises several first passage means, or bottom passage means, formed by apertures 331, each aperture having a substantially circular section, being formed in the wall of the second cylinder 3 in the bottom part 3a of said second cylinder. The apertures 331 allow a passage between the first channel 42 and the second channel 43.

In the example illustrated, the apertures 331 are formed regularly along a first circumferential ring 33 of the wall of the second cylinder.

The height difference H between the top ends of the first and second cylinders defines a second passage means, or top passage means 52.

A fluid can circulate in the photobioreactor 1, notably in the second channel 43 and in the first channel 42.

In this exemplary embodiment, the injection means 7 comprises several elements capable of injecting gas in the form of bubbles into the second channel 43. The injection means 7 comprises a compressor 72 for sending the gas and a membrane 71 capable of receiving the gas and injecting it in the form of bubbles. The membrane 71 is disposed inside the second cylinder 3. The compressor 72 is disposed below the photobioreactor 1.

The second cylinder 3 and the injection means 7 thus form an air lift system capable of injecting, into the photobioreactor, a gas, or a mixture of gases, or even a gas/solid mixture, and by so doing, drive the circulation of the fluid present in the second channel 43.

Depending on the applications, and notably the type of photobioreactor, the gas/solid mixture can be:
- an air/$CO_2$ gaseous mixture, and/or
- a gaseous mixture comprising solids, notably fine particles, and in particular microparticles to be treated.

The gas can be town air or industrial fumes, containing pollutants, including $NO_x$, which can pass in aqueous form (just like $CO_2$) and contribute to the supply of microalgae.

Hereinafter in the present description, the term gas will be used, it being understood that it can be a mixture of gases, or a gas/solid mixture.

The fluid is in particular a liquid, more particularly an aqueous solution comprising microalgae, also called "algal solution". However, the fluid can also define the mixture between the fluid and the gas, the gaseous mixture or the gas/solid mixture.

Hereinafter in the present description, the term fluid will be used, it being understood that it can be either the algal solution alone, or the mixture of said algal solution with the gas or with the gaseous mixture, or with the gas/solid mixture.

The main function of the membrane 71 is to inject the gas in the form of bubbles and above all more accurately control the size or sizes of said bubbles, the gas thus being diffused in the second channel 43 in the form of bubbles, thus making it possible notably to dissolve the gas, for example the $CO_2$, in the liquid. That can also help to increase the agitation in the reactor.

As an alternative to a membrane, it can be a diffuser of fine bubbles, a grating, a porous stone, a hydro-injector or any other means capable of injecting gas in the form of bubbles and of more accurately controlling the size or sizes of said bubbles.

There can be several membranes and/or other means capable of injecting gas in the form of bubbles. All are preferably disposed in the bottom part 3a of the second cylinder 3, and/or at several levels in said second cylinder along the longitudinal direction $Z_3$ of said second cylinder.

Figure 5:
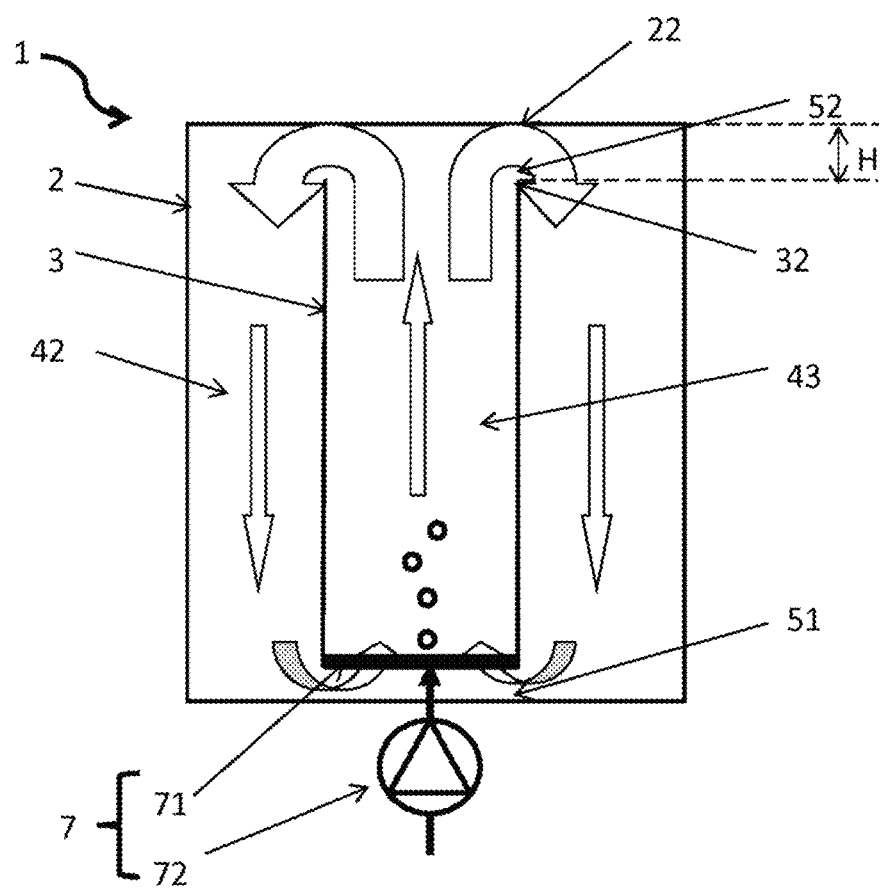
FIG. 5 illustrates the direction of circulation of the fluid in the photobioreactor according to the different embodiments.

FIG. 5 illustrates the direction of circulation of the fluid. The bubbles from the injection means 7, and in particular from the membrane 71, rise into the second channel 43 by driving the fluid present in said second channel. The duly driven fluid rises inside the second channel 43. Once the top end of said second channel is reached (corresponding in the example illustrated to the top end 32 of the second cylinder 3), the fluid pours into the first channel 42 by crossing the at least one top passage means 52, for example formed by the space due to a height difference between the first and second cylinders 2 and 3 at the top ends 22 and 32 of said first and second cylinders. Next, the fluid redescends to the bottom end of the first channel 42. At the bottom end of the first channel 42, the at least one bottom passage means 51, for example apertures 331 in the second cylinder 3, allow the suction of the fluid descending in the first channel 42 to the second channel 43 by virtue of the ascending flow of the second channel, the passage of the fluid once again into the second channel 43, and once again a fluid driving movement by the bubbles from the bottom part to the top part of the second channel 43, when the gas is injected.

The injection means 7 can inject bubbles of gas continually in the second channel 42.

Alternatively, the injection means 7 can inject bubbles of gas discontinuously.

Thus, a movement of the fluid is thus created, corresponding to a forced convection movement in the direction of circulation described above and illustrated in FIG. 5.

Furthermore, the photobioreactor comprises several light sources 8 represented in FIG. 1 in the form of several first light columns 810 disposed on the wall inside the second cylinder 3 and extending along the longitudinal direction $Z_3$ of said second cylinder. In the example represented, there are eight light columns 810 disposed regularly on the wall inside the second cylinder 3.

Other light source dispositions are presented more specifically with FIGS. 6, 7A, 7B, 8 to 11. All these dispositions can be combined with the photobioreactor illustrated in FIG. 1, or with the other embodiments presented hereinbelow.

Figure 2:
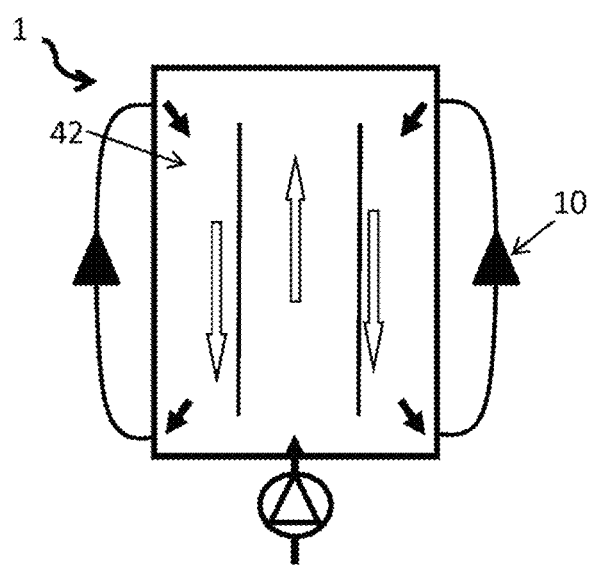
FIG. 2 illustrates a photobioreactor according to a second embodiment, comprising two recirculation pumps.

FIG. 2 illustrates a photobioreactor 1 according to a second embodiment, which is distinguished from the first embodiment in that it also comprises at least one recirculation pump 10.

Two recirculation pumps 10 are represented, disposed outside the first cylinder 2. Said pumps make it possible to accentuate the fluid circulation flow rate. They are configured so as to suck the fluid from the bottom part of the photobioreactor, for example in the bottom part of the first channel 42, and reinject it in the top part of the photobioreactor, for example in the top part of the first channel 42, accentuating the air lift phenomenon.

The number of pumps and the disposition of the pump or pumps can be adapted in order to make it possible to accentuate the fluid circulation flow rate.

Although all the elements of the photobioreactor have not been represented in FIG. 2, it is essential to consider that the photobioreactor of the second embodiment can comprise all or some of the elements described for the first embodiment.

Figure 3:
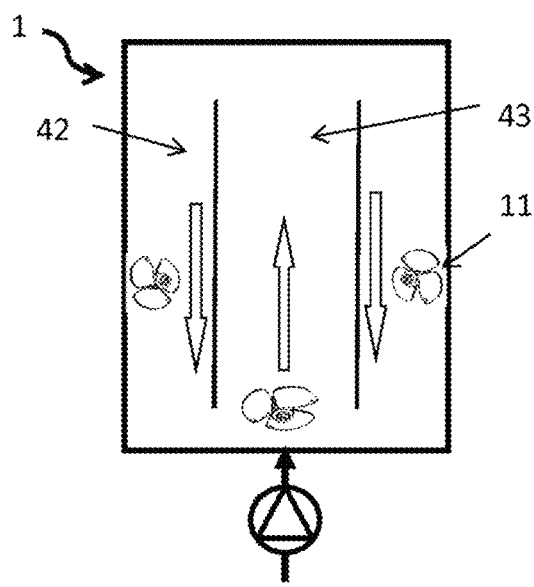
FIG. 3 illustrates a photobioreactor according to a third embodiment, comprising several propellers.

FIG. 3 illustrates a photobioreactor according to a third embodiment which is distinguished from the first embodiment in that it comprises at least one propeller 11.

According to the example represented, the photobioreactor comprises three propellers 11. One propeller is disposed in the bottom part of the second channel 43. A propeller is disposed and oriented in such a way that the propeller can apply an upward movement to the fluid from the bottom end to the top end of said second channel. Two other propellers are disposed in the first channel 42 so as to apply a downward movement to the fluid in said first channel from the top end to the bottom end of said first channel.

The propellers, driven by a motor disposed outside the photobioreactor 1, rotate and stir the fluid inside the photobioreactor. The propellers create a stirring which makes it possible to accentuate the stirring of the fluid in the photobioreactor.

The number of propellers and the disposition of the propeller or propellers in the photobioreactor can be adapted in order to obtain the same effect.

Although all the elements of the photobioreactor have not been represented in FIG. 3, it is essential to consider that the photobioreactor of the third embodiment can comprise all or some of the elements described for the first embodiment.

Figure 4B:
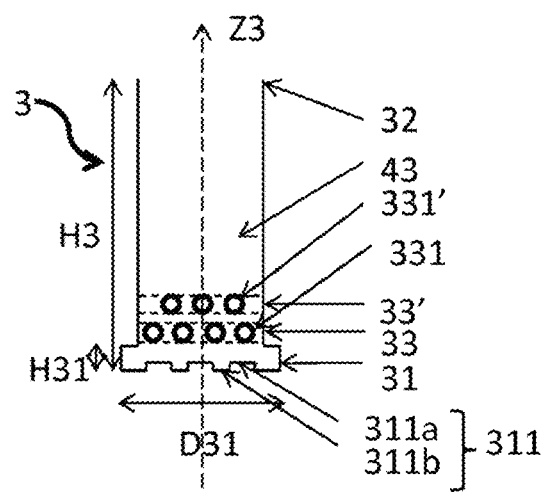
FIGS. 4A and 4B show a photobioreactor according to a fourth embodiment.
Figure 4A:
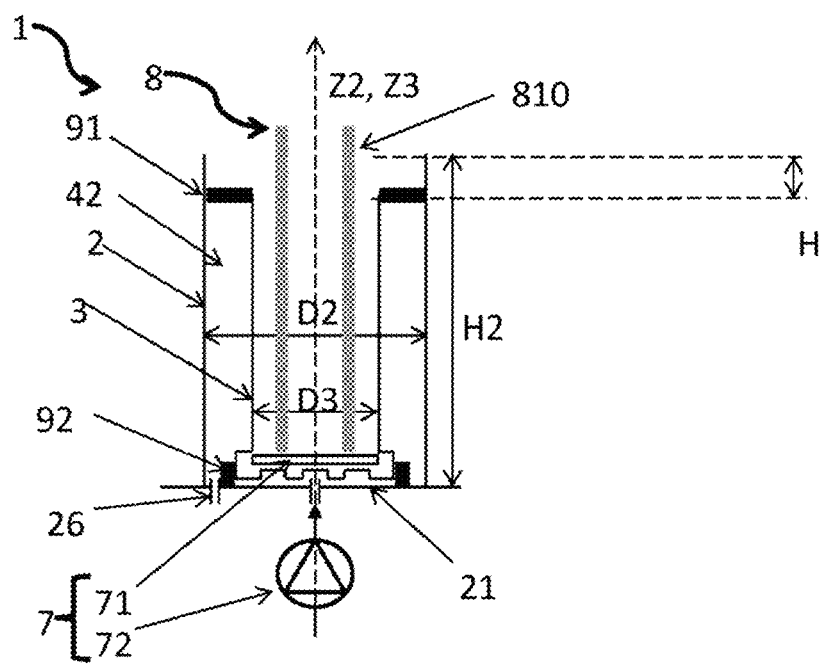

FIGS. 4A and 4B show an example of a photobioreactor according to a fourth embodiment.

FIG. 4A illustrates a photobioreactor 1 comprising a first cylinder 2 of revolution of first outer diameter D2 extending along a first longitudinal direction $Z_2$ over a first height H2 and a second cylinder 3 of revolution of second outer diameter D3 extending along a second longitudinal direction $Z_3$ over a second height H3. The two cylinders are hollow cylinders of revolution and are concentric.

The space between the two cylinders forms a first channel 42. The first channel 42 has a cylindrical sleeve form of a height equal to the height H3 of the second cylinder 3 and whose width corresponds to (D2−D3)/2 (and to (D2−D31)/2 at the level of the base 31 of the second cylinder, as explained hereinbelow).

The height H between the two cylinders forming a second passage means 52 is equal to H2−H3.

The photobioreactor 1 comprises holding means 9 capable of positioning and/or holding the second cylinder 3 relative to the first cylinder 2.

As an example, and as illustrated, the holding means 9 comprise holding cleats 91 disposed at the level of the top part 3b, preferably at the level of the top end 32 of the second cylinder 3, and capable of positioning the second cylinder 3 relative to the first cylinder 2.

Furthermore, they comprise centering cleats 92 fixed to the base 21 of the first cylinder 2 and capable of centering the second cylinder 3 relative to the first cylinder 2.

The lateral wall of the first cylinder 2 is made of transparent PVC, and its thickness is for example 10 mm.

The base 21 of the first cylinder 2 is made of non-transparent PVC and its thickness is for example 10 mm.

The base 21 of the first cylinder 2 is passed through by two passages 26, for example tappings, allowing a fluid or a fluid/solid mixture to arrive and/or leave inside said first cylinder.

The second cylinder 3 is disposed on the base 21 of the first cylinder 2, and is centered relative to said first cylinder by virtue of the centering cleats 92.

The base 31 of the second cylinder has a diameter D31 greater than the diameter D3 and comprises a bottom end in the form of notches 311, of which the protruding parts 311b are in contact with the base 21 of the first cylinder. The height of the bottom end is equal to H31. Each depression of a notch 311a can have a length L311a and a height H311a.

The depressions 311a of the notches can form first passage means for the fluid.

The injection means 7 comprises several elements capable of injecting gas in the form of bubbles into the second channel 43.

In this exemplary embodiment, the injection means 7 comprises a compressor 72 for sending the gas and a membrane 71 capable of receiving the gas and injecting it in the form of bubbles and diffusing it in the second channel 43. The compressor 72 is disposed below the photobioreactor 1.

The membrane 71 is disposed in the base 31 of the second cylinder 3. It takes the form of a flat disk of diameter D71.

FIG. 4B illustrates more specifically the second cylinder of revolution 3.

The lateral wall of the second cylinder 3 is made of transparent PVC, and its thickness is for example 5 mm.

The second cylinder 3 also comprises first passage means in the form: of first apertures 331 of diameters D331, disposed and distributed regularly along a first circumferential ring 33 in the wall of the second cylinder, at a height equal to H33 relative to the point of contact of the base 31 of said second cylinder with the base 21 of the first cylinder, and of second apertures 331' of diameters D331', disposed and distributed regularly along a second circumferential ring 33' in the wall of the second cylinder, at a height equal to H33' relative to the point of contact of the base 31 of said second cylinder with the base 21 of the first cylinder.

As an example, the abovementioned dimensions can be:
D2=400 mm
H2=3000 mm
D3=200 mm
H3=2525 mm
H=H2−H3=475 mm
D31=280 mm
H31=50 mm
D331=D331'=30 mm
H33=100 mm
H33'=200 mm
L311a=75 mm
H311a=22 mm
D71=270 mm Furthermore, the photobioreactor comprises several light sources 8 represented in the form of columns or tubes 810 in FIGS. 4A and 4B, but which can be configured otherwise, as presented hereinbelow.

Several light sources 8 can create a uniform light array by being spaced apart from one another by 10 cm.

According to an embodiment that is not represented, that can notably be applied to all the preceding embodiments, there can be several second containers 3 inside the first container 2. In this case, there can be several second channels 43.

That makes it possible to improve the uniformity of diffusion of the light within the algal liquid, increase the fluid circulation flow rate (reduction of the sections) and thus improve the homogenization of the medium, prolong the dwell time of the $CO_2$ bubbles in the medium and thus improve the rate of dissolution of $CO_2$ in the medium.

As indicated above, FIGS. 6, 7A, 7B, 8, 9, 10, 11 illustrate several light source dispositions.

The light sources are preferably distanced apart from one another by a maximum of 10 cm.

In the examples illustrated, the first container 2 is represented as being a cylinder of revolution, of longitudinal direction $Z_2$ and the second container 3 is represented as being a cylinder of revolution, of longitudinal direction $Z_3$.

To simplify the reading, in FIGS. 6, 7A, 7B, 8, 9, 10, 11, cylinders of revolution are represented and the corresponding description expresses first and second cylinders, it being understood that they can be containers which are not necessarily cylinders, and notably not necessarily cylinders of revolution.

The various light source dispositions can be combined with one another.

Furthermore, they can be combined with each of the different embodiments presented in conjunction with FIGS. 1 to 4B.

The lighting is preferably produced by LEDs, but other light sources can be envisaged. They can be spots, or festoons or light strips. Other embodiments are presented herein below.

The bubbles themselves can be light sources because they can diffract the light and return it to the fluid.

The intensity of the light sources must be appropriate: an excessively strong intensity risks roasting the micro-algae, and, on the other hand, an excessively low intensity makes them stick to the walls of the reactor.

Figure 6:
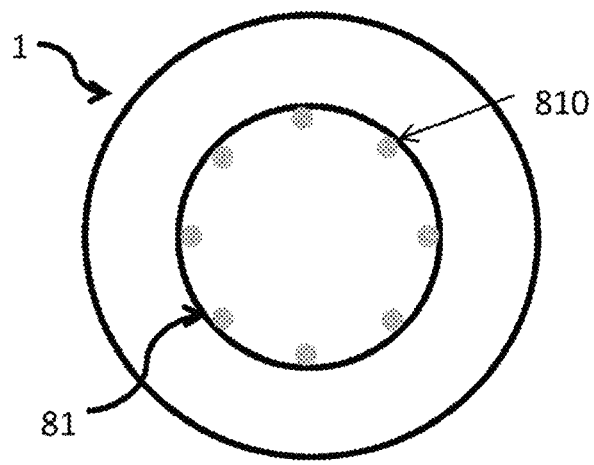
FIG. 6 illustrates a first example of placement of light sources.

FIG. 6 illustrates a first example in which the light sources 8 comprise first light sources 81 disposed inside the second cylinder 3.

They are illustrated in the form of first light columns 810 extending along the longitudinal direction $Z_3$ of the second cylinder 3.

The first light columns 810 are positioned on the internal lateral surface of said second cylinder, and are distributed regularly. In this example, eight light columns 810 are represented, but there can be fewer, or more.

The first light columns 810 can be fixed to a wall of the second cylinder 3, for example by a snap-fitting system.

In a photobioreactor in which the cylindrical walls are opaque, notably those of the second cylinder, it is important for the light sources to be able to diffuse the light at 360° and therefore for them not to be stuck to the walls of the cylinders.

Figure 7A:
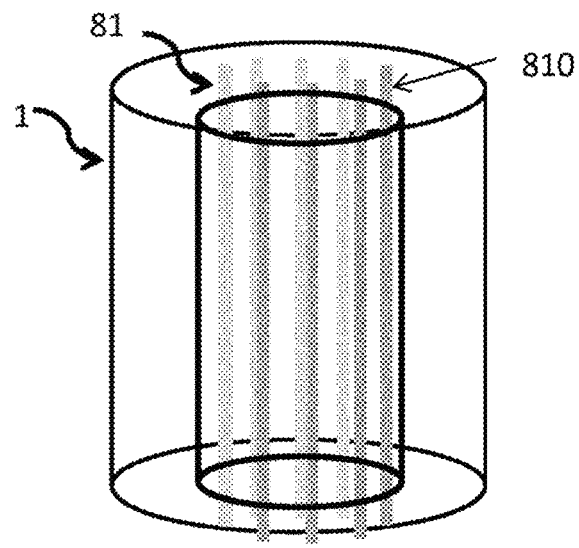
FIGS. 7A and 7B illustrate a second example of placement of light sources.
Figure 7B:
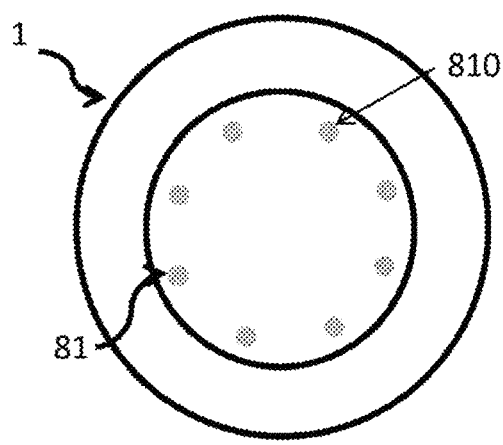

Thus, alternatively or in addition, the first light columns 810 can be positioned inside the second cylinder 3, but not on a lateral surface of said cylinder, as illustrated in FIGS. 7A (3D view) and 7B (plan view): second example of placement.

The spacing of the first light columns 810, and more broadly the spacing of the first light sources 81, with the internal lateral surface of the second cylinder 3, depends on the turbidity of the medium, on the concentration of algae, but also on the light intensity delivered.

Figure 8:
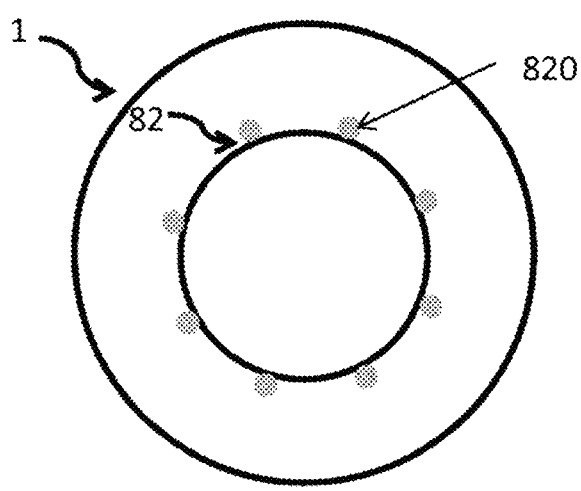
FIG. 8 illustrates a third example of placement of light sources.

Alternatively or in addition, second light columns 820 can be positioned between the first cylinder and the second cylinder, on the external lateral surface of the second cylinder 3 as illustrated in FIG. 8 in plan view (third example of placement).

Alternatively or in addition, second light sources 820 can be positioned between the first cylinder and the second cylinder, but not necessarily on the external lateral surface of the second cylinder.

Figure 9:
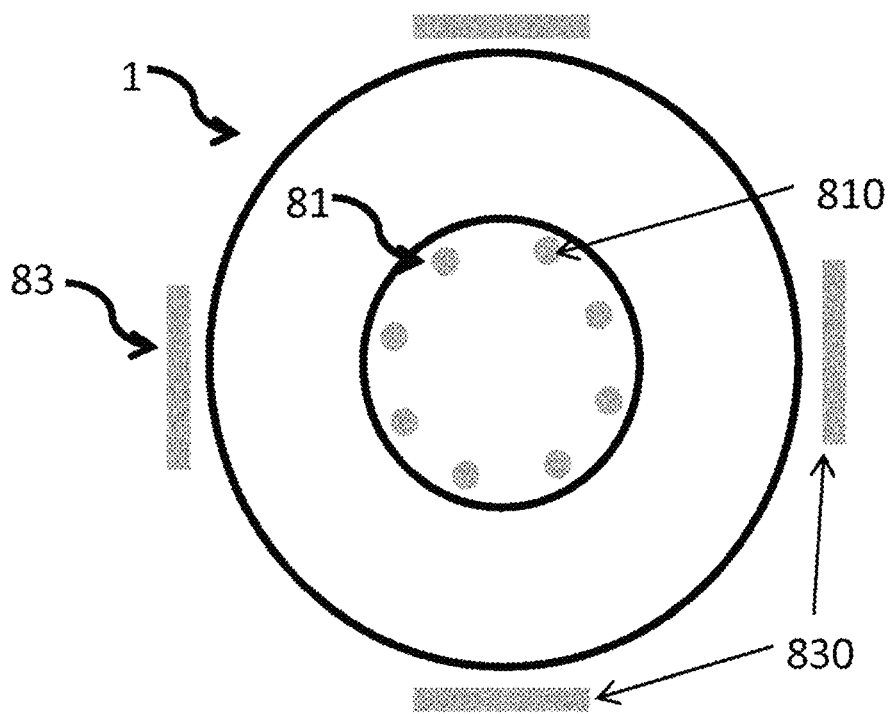
FIG. 9 illustrates a fourth example of placement of light sources.

FIG. 9 illustrates a fourth example of placement of light sources 8, in plan view.

In this example, first light sources 81 are disposed inside the second cylinder 3 and third light sources 83 are disposed outside the first cylinder 2.

The first light sources 81 are in the form of light columns 810 disposed inside the second cylinder 3.

The first light columns 810 extend along the longitudinal direction $Z_3$ and are positioned at a given distance from the internal lateral surface of the second cylinder 3. They can alternatively be disposed according to one of the first and third examples presented, or according to a combination of the first to third examples of placement.

The third light sources 83 are in the form of several second light columns 830 extending along the longitudinal direction $Z_2$ of the first cylinder 2. They can be positioned against the wall of the first cylinder 2 or at a distance D83 from the first cylinder 2.

The distance D83 between the third light columns 830 and the external lateral surface of the first cylinder 2, and more broadly between the third light sources 83 and said wall, depends on the turbidity of the medium, on the concentration of algae, but also on the light intensity delivered.

Figure 10:
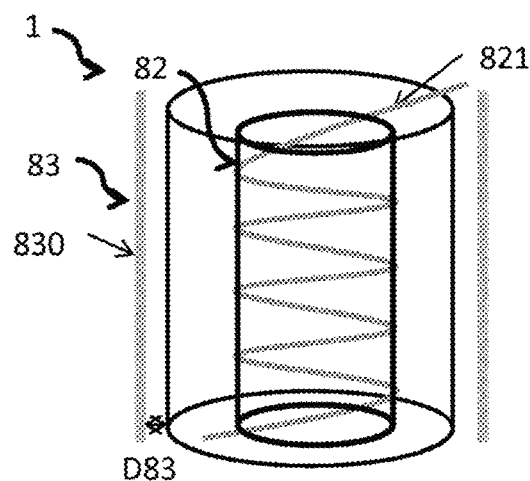
FIG. 10 illustrates a fifth example of placement of light sources.

FIG. 10 illustrates a fifth example of placement of light sources.

In this example also, second light sources 82 are disposed outside the second cylinder 3 and third light sources 83 are disposed outside the first cylinder 2.

As in the preceding example, the third light sources 83 are in the form of third light columns 830 extending along the longitudinal direction $Z_2$ of the first cylinder 2. They can be positioned against the external lateral surface of the first cylinder 2 or at a distance D83 from the first cylinder 2.

Alternatively, the third light sources 83 may not be incorporated.

The second light sources 82 comprise a second light coil 821 forming a helix whose axis corresponds to the longitudinal direction $Z_3$ of the second cylinder 3, disposed around the external lateral surface of said second cylinder.

Alternatively or in addition, a first light coil can be disposed inside the second cylinder 3.

Alternatively or in addition, a third light coil can be disposed outside the first cylinder 2.

The second, respectively first, light coil can be positioned on the external, respectively internal, lateral surface of said second cylinder or positioned at a given distance from said lateral surface.

The third light coil can be positioned on the external lateral surface of the first cylinder or positioned at a given distance from said lateral surface.

Figure 11:
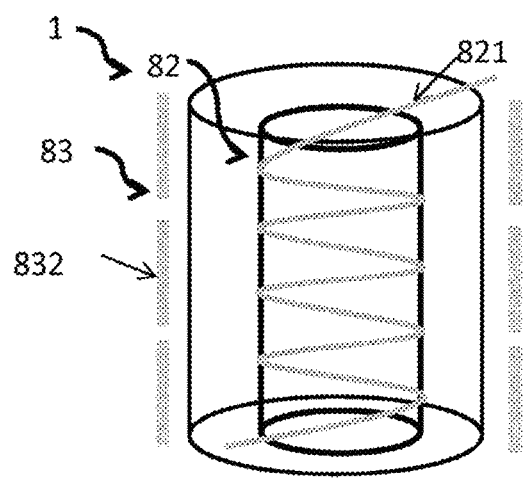
FIG. 11 illustrates a sixth example of placement of light sources.

FIG. 11 illustrates a sixth example of placement of light sources, which differs from the fifth example in that the third light sources 83 comprise light bar segments 832 extending along the longitudinal direction $Z_2$ of the first cylinder 2 and positioned outside said first cylinder.

The third light sources 83 can be positioned against the wall on the outside of the first cylinder 2 or at a distance D83 from the first cylinder 2.

The various embodiments presented can be combined with one another.

Furthermore, the present invention is not limited to the embodiments previously described but extends to any embodiment falling within the scope of the claims.

The invention claimed is:

1. A photobioreactor capable of containing at least one fluid, the photobioreactor extending between a bottom part and a top part, the photobioreactor comprising:
   a first container extending between a bottom end and a top end along a first longitudinal direction ($Z_2$);
   a second container extending between a bottom end and a top end along a second longitudinal direction ($Z_3$);
   the second container:
      extending inside the first container, so as to delimit a first channel between an internal lateral surface of the first container and an external lateral surface of the second container; and
      forming a second channel inside said second container;
   at least one first passage means capable of allowing the circulation of the fluid between the first channel and the second channel;
   at least one second passage means capable of allowing the circulation of the fluid between the first channel and the second channel and disposed above the at least one first passage means;
   at least one light source;
   a gas injection means, configured so as to inject gas in the form of bubbles into the second channel;
   the first and second containers, the first and second passage means and the injection means being configured so as to allow a circulation of the fluid in the photobioreactor between the first channel and the second channel, and the circulating fluid being able to be exposed to the at least one light source, the photobioreactor further comprising at least one recirculation pump configured to circulate the fluid from the bottom part of the photobioreactor to the top part of the photobioreactor.

2. The photobioreactor as claimed in claim 1, the first container being closed at the bottom end and the top end of said first container.

3. The photobioreactor as claimed in claim 1, the first and second longitudinal directions ($Z_2$, $Z_3$) of the first and second containers being parallel.

4. The photobioreactor as claimed in claim 3, the first and second containers being concentric cylinders of revolution.

5. The photobioreactor as claimed in claim 1, the at least one first passage means being formed by at least one aperture in a wall of the second container.

6. The photobioreactor as claimed in claim 5, the second container being a cylinder of revolution comprising a plurality of said at least one aperture forming the first passage means, disposed along at least one circumferential ring in the wall of said second container.

7. The photobioreactor as claimed in claim 1, the at least one first passage means being formed by notches disposed in a wall of said second container.

8. The photobioreactor as claimed in claim 1, the at least one second passage means being formed by a height difference between the first container and the second container, the top end of the second container being situated below the top end of the first container.

9. The photobioreactor as claimed in claim 1, the injection means being capable of generating bubbles of diameters less than or equal to 1 mm.

10. The photobioreactor as claimed in claim 1, the injection means being configured to inject a gas/solid mixture.

11. The photobioreactor as claimed in claim 1, the injection means being disposed below the second container.

12. The photobioreactor as claimed in claim 1, the injection means comprising at least one means capable of diffusing bubbles of gauged sizes.

13. The photobioreactor as claimed in claim 1, the at least one light source comprising at least one lighting wall out of at least one wall of the first and/or second containers.

14. The photobioreactor as claimed in claim 1, the photobioreactor comprising at least one propeller.

15. The photobioreactor as claimed in claim 1, wherein the at least one recirculation pump is configured to suck the fluid in the bottom end of the first channel, and to reinject said fluid in the top end of the first channel.

16. The photobioreactor as claimed in claim 1, the injection means comprising membrane disposed inside and in a bottom part of the second container.

17. A photobioreactor capable of containing at least one fluid, the photobioreactor extending between a bottom part and a top part, the photobioreactor comprising:
a first container extending between a bottom end and a top end along a first longitudinal direction ($Z2$);
a second container extending between a bottom end and a top end along a second longitudinal direction ($Z3$);
the second container extending inside the first container, so as to delimit a first channel between an internal lateral surface of the first container and an external lateral surface of the second container, and the second container forming a second channel inside said second container;
at least one first passage means capable of allowing the circulation of the fluid between the first channel and the second channel;
at least one second passage means capable of allowing the circulation of the fluid between the first channel and the second channel and disposed above the at least one first passage means;
at least one light source;
a gas injection means, configured so as to inject gas in the form of bubbles into the second channel;
the first and second containers, the first and second passage means and the injection means being configured so as to allow a circulation of the fluid in the photobioreactor between the first channel and the second channel, and the circulating fluid being able to be exposed to the at least one light source,
the photobioreactor further comprising at least one propeller disposed in the first channel so as to apply a downward movement to the fluid in said first channel from a top end to a bottom end of said first channel.

18. The photobioreactor as claimed in claim 17, further comprising at least one propeller disposed in the second channel, said propeller being oriented to apply an upward movement to the fluid from the bottom end to the top end of the second channel.

19. The photobioreactor as claimed in claim 17, the injection means comprising membrane disposed inside and in a bottom part of the second container.

* * * * *